United States Patent [19]
Maltby et al.

[11] Patent Number: 5,460,046
[45] Date of Patent: Oct. 24, 1995

[54] METHOD AND APPARATUS FOR ULTRASONIC PIPELINE INSPECTION

[75] Inventors: Philip M. Maltby, Tulsa; James S. Edwards, Sapulpa; John C. Hamilton, Tulsa, all of Okla.

[73] Assignee: TDW Delaware, Inc., Wilmington, Del.

[21] Appl. No.: 248,651

[22] Filed: May 19, 1994

[51] Int. Cl.6 .......................... G01N 29/24; G01N 29/10
[52] U.S. Cl. .............................. 73/623; 73/628
[58] Field of Search .......................... 73/623, 625, 628, 73/597, 622, 620; 376/245, 249, 252

[56] References Cited

U.S. PATENT DOCUMENTS

| | | | |
|---|---|---|---|
| 3,732,625 | 5/1973 | Vernooy | 33/623 |
| 3,755,908 | 9/1973 | Vernooy | 33/178 F |
| 3,810,384 | 5/1974 | Evans | 73/623 |
| 3,862,497 | 1/1975 | Vernooy et al. | 33/141 G |
| 4,285,243 | 8/1981 | Collingwood | 73/623 |
| 4,522,063 | 6/1985 | Vernooy | 73/579 |
| 4,560,931 | 12/1985 | Murakami et al. | 73/623 |
| 4,641,520 | 2/1987 | Mao | 73/597 |
| 4,780,962 | 11/1988 | Smith | 33/523 |
| 4,909,091 | 3/1990 | Ellmann et al. | 73/623 |
| 4,964,059 | 10/1990 | Sugaya et al. | 73/623 |
| 5,285,689 | 2/1994 | Hapstock et al. | 73/623 |

*Primary Examiner*—Hezron E. Williams
*Assistant Examiner*—Rose M. Finley
*Attorney, Agent, or Firm*—Head and Johnson

[57] ABSTRACT

A method and an apparatus are provided for measuring the wall thickness of a pipeline through which a fluid flows, the pipeline having an interior and exterior surface. The apparatus has a pig body supported by elastomeric cups to thereby cause the pig body to move by fluid flow through the pipeline. The pig body supports a plurality of multi-element transducers. Each transducer is made up of a large number of independent elongated rod-like crystal elements separated by a polymer, each having side walls, a front face and a bottom face. The rod-like elements are arranged so that the side walls are adjacent but mechanically isolated from each other, such as by an epoxy, with the front faces and bottom faces providing transducer front and bottom surfaces. A front metallic film and a bottom metallic film are applied to the front and the bottom surfaces. Each transducer is configured to have an impedance that closely matches the impedance of the pipeline fluid. Each transducer is activated by periodic electrical pulses to cause transmission of an acoustic signal in the pipeline fluid that are reflected by the pipeline interior and exterior walls. A plurality of multiple ultrasonic reflections from the pipe interior and exterior walls for each ultrasonic pulse produced by each transducer is analyzed employing a software algorithm embedded in the electronics within the pig body to provide a measurement of pipe wall thickness. By means of an odometer attached to the pig body, electrical signals are provided that reveal anomalies in the wall thickness of the pipeline relative to the distance traveled by the pig body so that an operator can thereby determine the location in the pipeline wall thickness anomalies.

8 Claims, 9 Drawing Sheets

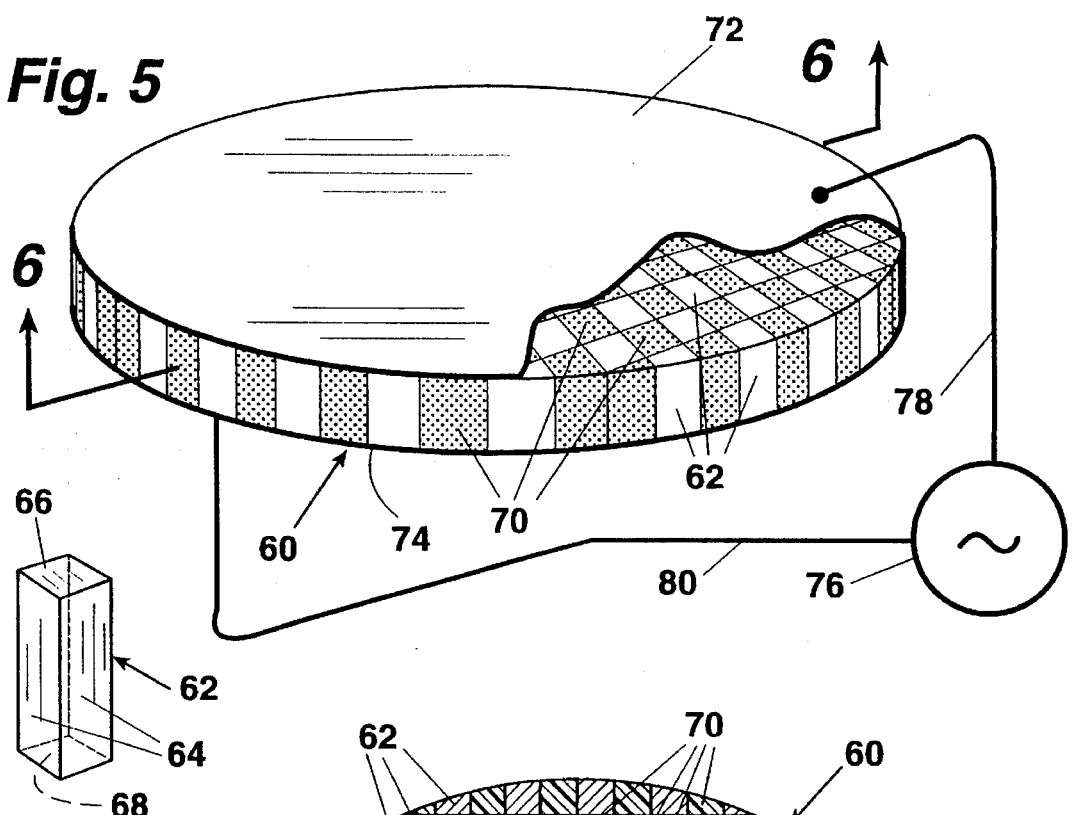
Fig. 5
Fig. 5A
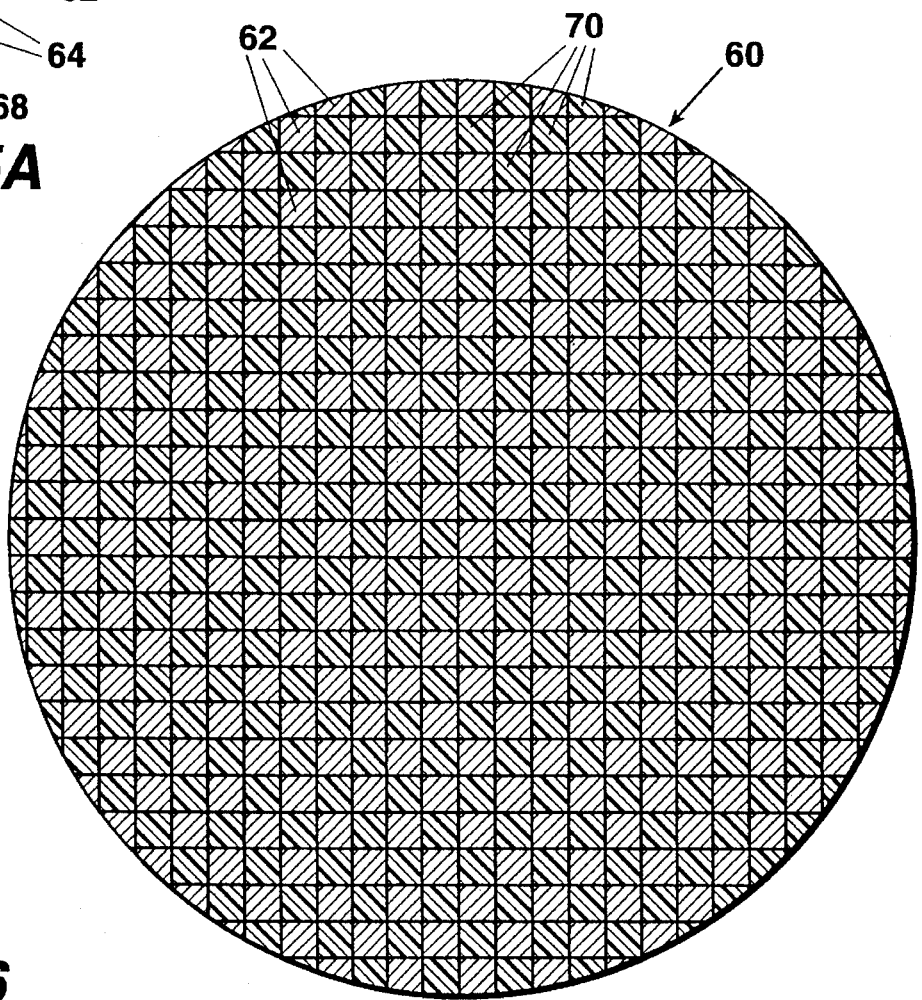
Fig. 6

$Z_t \gg Z_c$

ALL ENERGY REFLECTED TO TRANSDUCER (NO ENERGY TRANSMITTED TO COUPLANT)

$Z_t > Z_c$

SOME ENERGY REFLECTED TO TRANSDUCER AND SOME ENERGY TRANSMITTED TO COUPLANT $Z_t = Z_c$

NO ENERGY REFLECTED TO TRANSDUCER (ALL ENERGY TRANSMITTED TO COUPLANT)

$Z_t$ = TRANSDUCER ACOUSTIC IMPEDENCE
$Z_c$ = COUPLANT ACOUSTIC IMPEDENCE

METHOD AND APPARATUS FOR ULTRASONIC PIPELINE INSPECTION

CROSS-REFERENCE TO RELATED APPLICATIONS

This application is not related to any pending patent applications.

CROSS-REFERENCE TO MICROFICHE APPENDIX

This application is not related to any microfiche appendix.

BACKGROUND OF THE INVENTION

Piezoelectric ultrasonic transducers have been utilized in in-line pipeline inspection since the mid-1980's. Specifically, the use of piezoelectric transducers for pipeline inspection is disclosed in U.S. Pat. No. 3,810,384, issued May 14, 1974, entitled "Ultrasonic Pipeline Inspection Device". The teachings of this patent are incorporated herein by reference.

In the system described in this patent, transducers are used for making measurements of the remaining wall thickness of in-service pipelines. While improvements have been made to existing inspection systems, the use of piezoelectric devices for this application remains a challenge. Typically, the transducers are mounted in a mechanical holder so that a relatively constant distance is maintained between the face of the transducer and the inside of the pipeline wall. The mechanical mounting arrangement is then moved through the pipeline as a part of another vehicle commonly known in the industry as a "pig". The transducers must operate in the pipeline environment to make measurements in determining the mechanical integrity of the pipeline. Pipelines frequently carry liquids or gases at pressures of 100 psi to 2000 psi. A wide variety of different materials are conveyed by pipelines, including caustic compounds, petroleum products containing acids, liquified petroleum products (LPG), carbon dioxide and dry gaseous materials. Further, the temperature of products conveyed by pipelines can vary widely. Of critical importance to the pipeline operator are the effects of corrosion damage to the pipeline. Consequently, it is common to measure the thickness of the pipe wall around the entire periphery of the pipe and at short intervals along the length of the pipeline. In the event that corrosion has taken a toll on the pipe wall, the measurements made by the ultrasonic transducers will indicate that the wall is thinner in the affected zones than it is where no corrosion is present. Although the inspection system is controlled by sophisticated computer based electronics, the performance of the ultrasonic transducers is critical to acquisition of meaningful inspection data.

Piezoelectric transducers are manufactured by mechanically configuring ceramic material to provide a natural frequency of vibration compatible with the testing necessary for the pipeline. Ordinarily a transducer crystal is produced in the form of a thin circular wafer. When a short duration voltage (pulse) is applied between the front and back surfaces of the wafer, it responds by changing its physical dimensions and consequently, experiences a mechanical vibration. The physical nature of the crystal vibration is controlled by the elastic properties of the piezoelectric material and its geometric dimensions. The frequency of the resulting vibration is called the natural frequency of the crystal. When placed in proximity to another elastic material, it can stimulate the propagation of acoustic energy in that material. Acoustic energy is propagated according to the physical theory governing the transmission of waves in elastic media. The normal process for stimulating elastic waves in a material undergoing nondestructive testing is to couple the transducer to the specimen material via a fluid. Nondestructive testing done in this manner is sometimes called direct contact testing. Direct contact testing is used during external pipe wall testing. If the pipe has been buried it has to be excavated for direct contact testing at considerable expense. Among the common fluids used in standard thickness testing is glycerin and silicon oils. These "couplants" are usually quite viscous with the consistency of a heavy grease. These are unsuitable for the in-line inspection of pipelines because of their viscosity. Therefore, other materials must be utilized for this purpose.

Clearly, during the process of inspecting a pipeline, it is convenient to use the materials that are ordinarily transported by the pipeline. In petroleum related transportation systems, the materials range from heavy crude oils to natural gas. The piping industry desires to inspect all kinds of pipelines regardless of the materials that are being transported. Unfortunately, existing commercial inspection systems utilizing ultrasonic transducers perform satisfactorily only in certain liquid pipelines. The reason for this limitation is based on the nature of piezoelectric transducers. Specifically, difficulty arises from the differences in physical properties of the transducer and the pipeline materials. All physical materials exhibit a property known as acoustic impedance. This property, for practical purposes, is specified by the arithmetic product of the material density and the speed with which sound is propagated in the material. It is well known that the acoustic impedance of piezoelectric ceramics is considerably higher than that of virtually all fluids commonly transported in pipelines. The impedance mismatch results in a variety of difficulties when trying to use monolithic piezoelectric devices as pipeline inspection transducers where many different pipeline fluids are involved. Acoustic impedance is analogous to electrical impedance and it is well known that, between two electrical circuits, maximum power transfer occurs only when the impedance of the driven circuit matches the output impedance of the driver circuit. When the impedance is complex, the input impedance of the receiving circuit must be the complex conjugate of the output impedance of the driver. Also, the mathematical models for acoustic transmission verify that maximum acoustic energy is transmitted between two acoustic media when the two media have identical acoustic impedance's.

A commonly used ceramic piezoelectric material is PZT (Lead Zirconate Titanate) and this material has an acoustic impedance of about 30 MRayl (1 MRayl-$10^6$ kg/m$^2$-sec). Many pipeline liquids have approximately the same acoustic impedance as water which is about 1.5 MRayl. This means that the transducer/water impedance ratio is about 20:1 which is a significant mismatch and results in a large part of the acoustic energy produced by the transducer being reflected back into the transducer. Additional problems include narrow bandwidth and minimal damping. However, in spite of these serious drawbacks, sufficient energy is transmitted to the liquid to make in-line pipeline inspection practical.

The pipeline liquid is called a couplant since it is the means by which the acoustic energy emitted by the transducer is "coupled" to the steel pipe wall. So, while the transducer/liquid match is not ideal, it is close enough to be useful with certain fluids. In a typical pipeline inspection configuration, the transducers are directed normal (perpendicular) to the pipe wall and are positioned such that the transducer face is in the range of 0.5" to 1.5" from the inside pipe surface. It is critical that the transducers be efficient at producing and receiving ultrasonic energy because a considerable part of the acoustic energy never enters the couplant. Also, pipe wall abnormalities will scatter some of the acoustic energy and there is significant signal attenuation in the couplant.

In most practical ultrasonic pipeline inspection systems, transducers are utilized as both a transmitter and a receiver of acoustic energy. This is accomplished by the so-called "front-end" electronics which connects the transducer terminals to a high-power driver amplifier during the transmit interval and then switches the transducer terminals to a high gain, low noise amplifier during the receive interval. Generally, a transducer that exhibits poor characteristics as either a transmitter or a receiver will also be inefficient at the other task.

If the effectiveness of energy transfer between the transducer and the couplant is less than ideal for liquid couplants, it is next to impossible when the couplant is air or gas. The acoustic impedance of air at standard temperature and pressure is approximately $4 \times 10^{-4}$ MRayl. This means that the ratio of the acoustic impedance of PZT to that of air, under these conditions, is about $7.5 \times 10^4$. This extreme difference in acoustic impedance's results in virtually all of the acoustic energy produced by the transducer being reflected back into the transducer. Because no energy is propagated into the couplant, there is no means for acquiring reflected energy from the pipe wall. Thus, the inspection of gas transmission pipelines has not proven to be practical with monolithic piezoelectric transducers.

This application is based on the discovery that specifically configured, multi-element ultrasonic transducers exhibit characteristics of lower density, thus lower acoustic impedance, with increased elastic compliance that make them compatible with conditions associated with the ultrasonic inspection of pipelines. It has been discovered that by effectively arranging a large number of small piezoelectric elements in an array such that all elements are electrically driven from a single source an assembly is provided that exhibits properties analogous to the multi-element arrays used in advanced radar systems.

Multi-element transducers have been evaluated by substituting them in place of the monolithic devices that are ordinarily used in pipeline equipment. Their performance in the pipeline environment was found to be unexpectedly superior to that of conventional monolithic transducers. Further, investigation revealed that improved performance has resulted from the fact that multi-element transducers can be fabricated in such a manner that their acoustic impedance's more nearly match that of the common liquids transported in pipelines. Indeed, this disclosure is based on the discovery that the physical configuration of multi-element transducers is such that the devices can be tailored to provide closer acoustic impedance matches to all pipeline fluids from heavy crude oils to gases. Utilization of multi-element transducers makes it possible to design transducers for every type of pipeline fluid.

Ultrasonic pipeline inspection ordinarily involves the measurement of the thickness of the remaining pipe wall. This means that, if no metal loss has occurred in the pipe wall due to corrosion or other mechanical damage, the instrumentation associated with the ultrasonics system will indicate normal wall thickness. However, if metal loss has occurred, the system will record information that indicates that the pipe wall is now thinner than that of the original, undamaged pipe. Traditionally, the ultrasonic process has been to simply measure the time the ultrasonic energy takes as it enters the pipe wall, reflects from the outer wall and returns to the transducer. For this measurement, the reference is the first reflection from the inside pipe wall (ID) surface. The next signal received from the transducer is ordinarily the reflection from the outside (OD) pipe wall. The time difference from the beginning of the ID signal to the start of the OD signal represents the time taken for the ultrasonic energy to traverse the pipe wall twice. This is commonly called two-way time and in pipeline inspection parlance it is often called "metal time" because it represents the time the ultrasonic energy takes to traverse the steel wall of the pipe. Using half the metal time (one-way time) the pipe wall thickness is readily computed because the velocity of sound in steel (approximately 5,793 m/sec.) is known.

Applicants have determined that this conventional method for measuring pipe wall thickness is generally unsuitable for use in pipeline inspection. For example, this technique is inappropriate for determining if a metal loss defect is internal or external to the pipe. There are many other uncertainties that arise when trying to use the conventional method for wall thickness measurement. Extensive laboratory and field testing has demonstrated that the validity of the wall thickness measurement process is dramatically improved if multiple metal times are utilized in an appropriate computer processing algorithm. Multiple metal times are produced in the ultrasonic wall thickness measurement process because of the significant acoustic impedance contrasts between the steel pipe wall and the couplant on the inside of the pipe and air or pipe coating on the outside of the pipe. The magnitude of each successive metal time pulse is reduced exponentially. The reduction of the signal amplitude is caused by a combination of the interface impedance contrasts and attenuation in both the steel and the couplant. This is readily modeled mathematically as a decaying exponential function and the time constant controls the rate of decay of the signal amplitude. The significance of the metal time amplitude decay is that the signal to noise ratio must be acceptable for the last metal time used in an analysis. For example, if five metal times are used in an analysis algorithm in order to facilitate the final interpretation process, the last metal time must still be well above a threshold that exceeds the background noise in order to be used in the algorithm.

While conventional monolithic piezoelectric transducers have provided usable multiple metal time signals for the analysis algorithm, the results are often less than satisfactory and, for some pipeline fluids, the results have not proven to be satisfactory. The signal is often so small, even after two metal times, that background noise causes difficulty with the analysis algorithm and a meaningful wall thickness measurement cannot be made.

In trying to improve upon the signal to noise ratio inherent in conventional monolithic piezoelectric transducer, applicants have discovered that multi-element transducers significantly improve the signal to noise ratio so that multiple metal times can be used in the analysis algorithm. Therefore, by using multi-element transducers, a significantly larger number of wall thickness measurements can be made. Indeed, multi-element transducers have been found to improve the sensitivity of the transmit/receive process by nearly 10:1 (20 db). Perhaps of even more significance, the decay time (time constant) of the successive metal time pulses has been improved so that many more metal times can be utilized without significant problems with signal to noise ratios.

BRIEF SUMMARY OF THE INVENTION

This invention provides a method and apparatus for ultrasonic pipeline inspection. The method and the apparatus produces a record of measurements that can be used to determine the characteristics of the wall of a pipe, such as in a pipeline, the characteristics of the wall of a pipe being primarily the pipe wall thickness.

An instrument pig is passed through the interior of a pipeline having fluid media flowing therein. The fluid media can be such as water, salt water, crude oil, gasoline, liquid fertilizer, natural gas, and so forth, that is, the full gamut of fluids that are customarily moved from one geographical location to another through a pipeline. By means of a plurality of spaced apart multi-element transducers carried by the instrument pig, a sequence of transducer initiated ultrasonic pulses are generated. Each ultrasonic pulse is coupled from a multi-element transducer to the fluid media in the pipeline and thereby to the pipeline interior wall. The ultrasonic pulse travels through the pipeline from the interior wall to the exterior wall. A portion of the acoustic pulse is reflected by both the pipeline interior and exterior wall, thus providing interior and exterior pipeline wall reflected acoustic pulses. These reflected pulses are coupled by the fluid media back to the transducer.

The transducer, in response to receipt of reflected acoustic pulses, generates electrical signals as a consequence of said interior and said exterior pipe wall reflected acoustic pulses. By employment of circuitry carried by the instrument pig, the electrical signals indicative of the reflected acoustic interior and exterior wall pulses provide information as to the wall thickness.

Each of the multi-element transducers is made of a plurality of discrete piezoelectric crystals that are in the form of rod-like elements, the crystal elements being separated by a polymer. These discrete rod-like piezoelectric elements each have side walls, a forward face and a rearward face. The discrete rod-like piezoelectric elements are arranged so that their side walls are mechanically isolated from each other with a polymer. The major surfaces are lapped flat and a common electrode is applied over the individual elements. The front faces of the plurality of discrete rod-like piezoelectric elements and polymer present a common surface and the rear faces, likewise, present a common surface. A first conductive film is in electrical continuity with each piezoelectric rod-like element forward face and, in like manner, a second conductive film is applied to the rearward face. Conductors extend from the first and second conductive films to circuitry, the conductors providing means for transmitting from the circuitry to the multi-element transducer an electrical signal to initiate an ultrasonic pulse and, in like manner, to transmit from the multi-element transducer electrical signals back to the circuitry indicative of ultrasonic pulses reflected from the pipe interior and exterior walls.

In a preferred practice of the invention, each of the multi-element transducers is arranged so that each produces an ultrasonic pulse of a magnitude to cause an interior reflection and a sequence of reflections of the ultrasonic pulse from the pipeline interior and exterior walls. Upon striking the interior pipe wall a portion of the ultrasonic energy is reflected back toward the transducer while remaining energy propagates through the pipe wall towards the exterior pipe wall. When reaching the external pipe wall, a portion of the ultrasonic energy is reflected back towards the transducer. Thus, for each ultrasonic pulse produced by each of the transducers, a pulse train of ultrasonic wave forms is generated from an ID echo and multiple OD echoes. As each pulse is received by the transducer it is converted into an electrical signal by the transducer. Wave forms contained in the pulse train are indicative of pipe wall thickness. By analyzing the multiple interior and multiple exterior pipe wall reflections, the thickness of the pipe wall can be more accurately determined in response to each ultrasonic pulse produced by each of the multi-element transducers.

A better understanding of the invention will be obtained from the following detailed description and claims taken in conjunction with the attached drawings.

DESCRIPTION OF THE DRAWINGS

FIG. 4 is taken along the line of 4—4 of FIG. 3.

FIG. 5 is a diagrammatic isometric view of a multi-element crystal component of a transducer as illustrated in FIGS. 3 and 4. This figure shows the method of providing an electrical pulse to the transducer for initiating an ultrasonic signal.

FIG. 5A is an isometric view of a single rod-like crystal element of which the multi-element transducer of FIG. 5 is composed.

FIG. 6 is an enlarged cross-sectional view, taken along the line 6—6 of FIG. 5, of the multi-element transducer of FIG. 5.

FIG. 12 shows the effect on instrumentation having the ability to distinguish the signals above the background noise level, that is, showing the advantage of being able to distinguish a plurality of signals that are of sufficient amplitude to be detectable over background noise. In the illustration of FIG. 12, Pulse 6 is within the background noise level and would not be useable in calculating pipe wall thickness.

DESCRIPTION OF THE PREFERRED EMBODIMENTS

Figure 1:
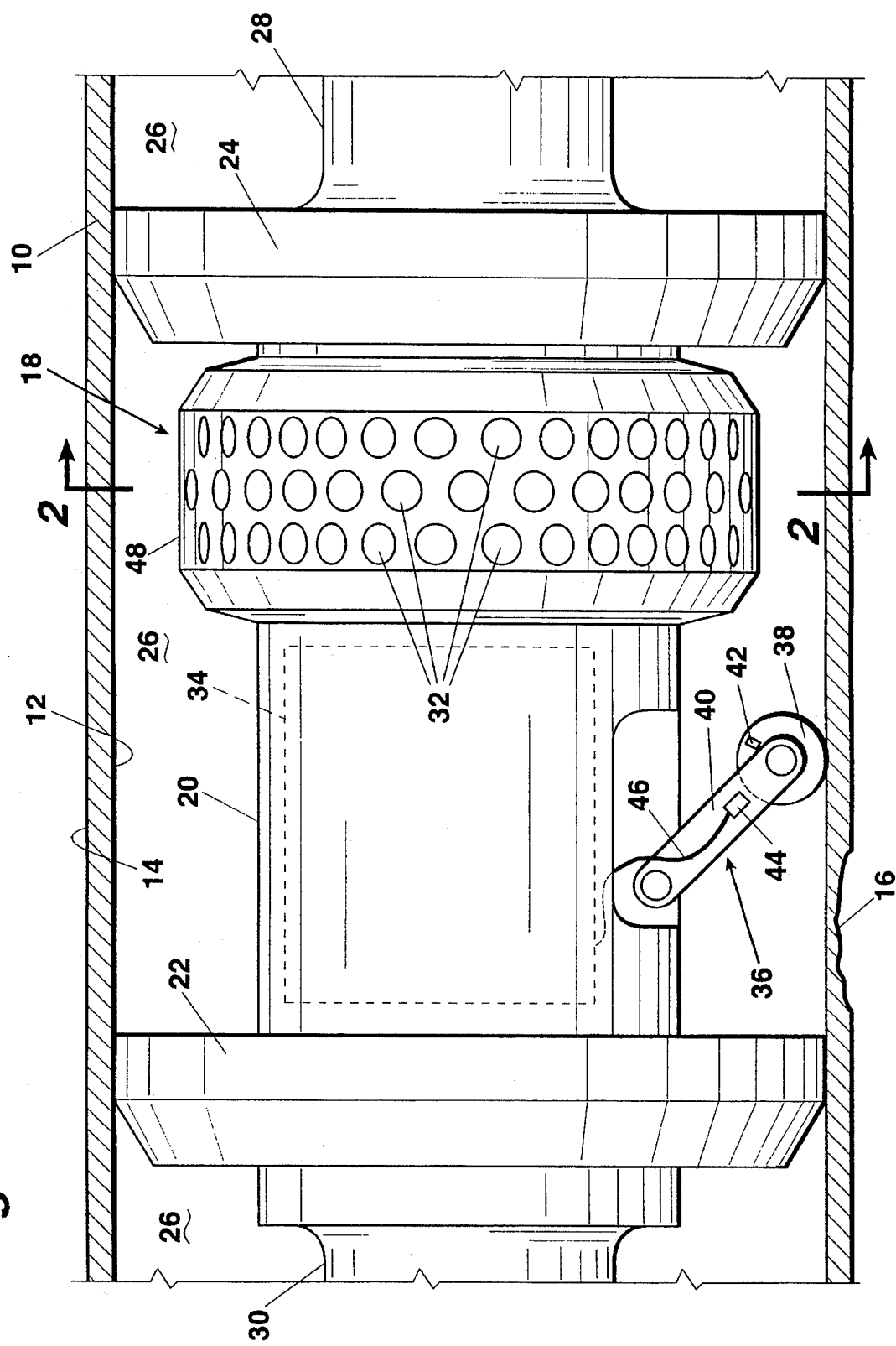
FIG. 1 is a elevational cross-sectional view of a portion of a length of pipe, such as a pipeline, and showing portions of an instrument pig positioned in the pipeline. The instrument pig has elastomeric cups which serve to support the pig in the pipeline and to cause the pig to move by fluid flow through the pipeline. The instrument pig of FIG. 1 is illustrated diagrammatically as indicative of a pig having means to support a plurality of multi-element transducers, instrumentation, and an odometer to provide information about the wall thickness of the pipe.

Referring to the drawings and first to FIG. 1, a section of the length of pipe 10 is shown. Pipe 10 is representative of a pipe typically employed in a pipeline and is usually formed of steel. Pipe 10 has an inner wall 12 and an outer wall 14. Provided herein is a method and apparatus for inspecting pipe 10 and particularly, for measuring the thickness of the pipe wall, that is, the distance between inner wall 12 and outer wall 14. When pipe 10 is employed in a pipeline it typically has a highly uniform pipe wall thickness. However, due to age, poor maintenance, formation of acids due to the medium being transported by the pipeline, erosion and ph of surrounding ground, corrosion, particularly galvanic or to mechanical damage or the like, the thickness of the pipe wall can change. An area of corrosion is illustrated by the numeral 16 wherein the pipe wall thickness has substantially decreased. Corrosion can occur either interiorly or exteriorly of a pipe wall but is more often characteristic of changes in the exterior of the pipe wall since the exterior is exposed to soil moisture with any corrosive chemicals it may contain and to the effect of galvanic action. In any event, and for whatever the cause, pipeline operators need to know when changes occur in the thickness of a pipe wall since if the changes are sufficient to impair the integrity and safety of the pipeline, so that corrective action can be taken.

Positioned within the interior of pipe 10 is a pipeline pig transducer ring 18. Mechanical fastening, array positioning, and electrical communication for multi-element transducers are functions of the transducer ring 18. Transducer ring 18 is an integral part of the pipeline pig 18 being generally referred to as an "instrumentation pig", that is, a pig intended to provide information rather than to provide a mechanical service, such as separating one fluid component from another.

The pipeline pig 18 includes a body 20 that is supported between elastomeric cups 22 and 24. The function of cups 22 and 24 is to support pig body 20 coaxially within the interior pipe wall 12 and to impede the flow of fluid 26 flowing through the pipeline so as to cause pig 18 to move with the fluid flow through the pipeline.

Pipeline pig 18 is illustrated with a rearward component 28 and forward component 30 that may be used for other purposes not related to that of this disclosure.

Mounted on an exterior circumferential surface of transducer ring 18 is a 360° array of multi-element transducers 32. One function of each multi-element transducer 32 is to convert electrical energy into acoustic energy. Another function is to convert acoustic energy into electrical signals. Acoustic energy generated by each multi-element transducer 32 is relayed and propagated through pipeline fluid 26 to pipe interior wall. Efficiency of acoustic energy relayed into fluid 16 from the multi-element transducers 32 impedance matching layer (FIG. 3 number 86) is largely due to congruency of acoustic impedance between a transducer and pipeline fluid 16, i.e., the closer the acoustic impedance match the greater the efficiency. The control of transducers 32 and the utilization of information obtained from the transducers is carried out in instrumentation 34 positioned within the interior of pig body 20.

Affixed to pig body 20 is an odometer, generally indicated by the numeral 36. The use of odometers in connection with instrumentation pigs is well known, and the odometer herein is illustrated diagrammatically. Essentially the typical odometer includes a wheel 38 that engages interior pipe wall 12 and rotates as the pig moves through the pipeline. Wheel 38 is supported by an arm 40 that is hinged to pig body 20. Wheel 38 carries a magnet 42 that is detected upon each revolution of wheel 38 by a magnetic sensor 44. By means of conductor 46, information as to the rotational of wheel 38 is conveyed to instrumentation 34. For more detailed information as to the function and operation of pipeline pig odometers, reference may be had to the following United States Patents.

| U.S. Pat. No. | TITLE |
| --- | --- |
| 3,732,625 | Pipeline Pig |
| 3,755,908 | Pipeline Pig |
| 3,862,497 | Pipeline Pig |
| 4,522,063 | Methods and Apparatus For Indicating Selected Physical Parameters In a Pipeline |
| 4,780,962 | Pipeline Bend Verification Pig |

Transducers 32 are supported in an enlarged diameter portion 48 of the pig body. The transducers need to be supported fairly close to pipeline interior wall 12 and in a manner so that the spacing between transducers 32 and the pipeline interior wall 12 remains substantially consistent as the pig 18 moves through the pipeline. The spacing between transducers 32 and pipeline interior wall 12 is typically from about ½"–2" with about 1 ½" being representative. The spacing should be as close as practically possible to diminish the attenuation of acoustic pulses that travel in fluid 26 between the pipe wall and each transducer but, at the same time, transducers 32 must be spaced far enough away from the pipe wall that they will not be damaged by any changes in configuration of the pipe wall, such as bends and reduced pipe ID due to heavy wall pipe, as pig 18 moves through the pipeline.

Figure 2:
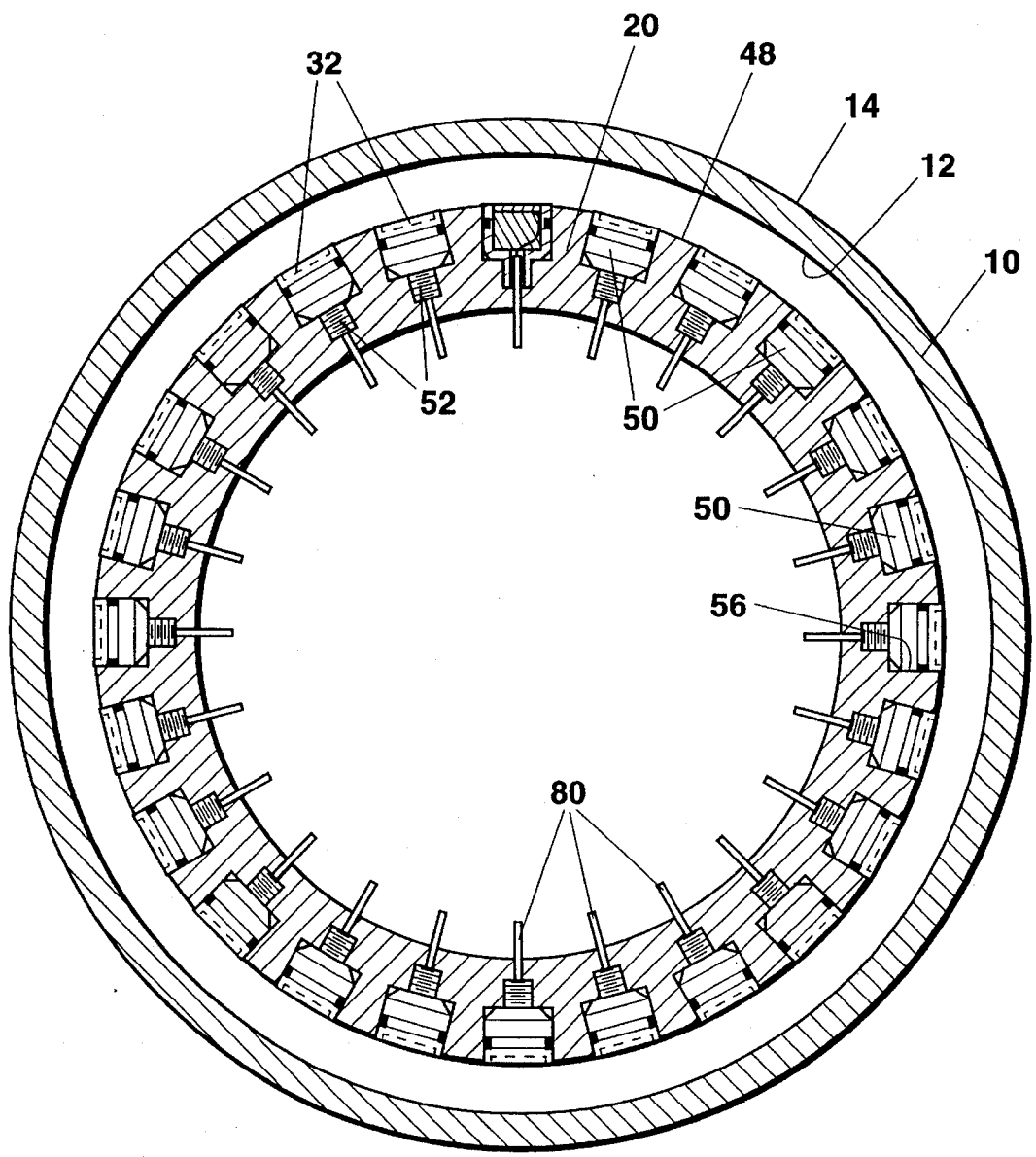
FIG. 2 is a cross-sectional view, taken along the line 2—2 of FIG. 1, showing a portion of the instrumentation pig in cross-section and showing placement of some of the multi-element transducers that are employed for providing a record that can be used to determine characteristics of the wall of the pipe.

FIG. 2 is a cross-sectional view of enlarged diameter section 48 of the pig body and shows how a plurality of transducers 32 are mounted in spaced apart relationship around the full parameter of the pig body.

Figure 3:
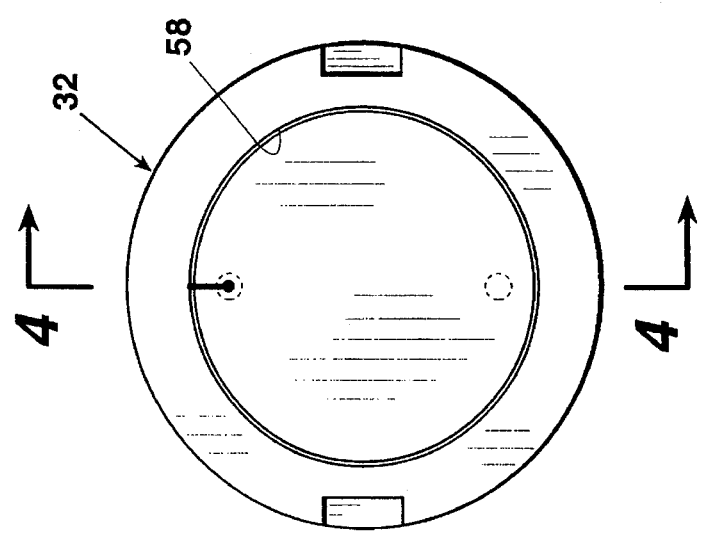
FIG. 3 is a plan view of the forward face of a multi-element transducer, a plurality of which is employed in the instrument pig of FIGS. 1 and 2.
Figure 4:
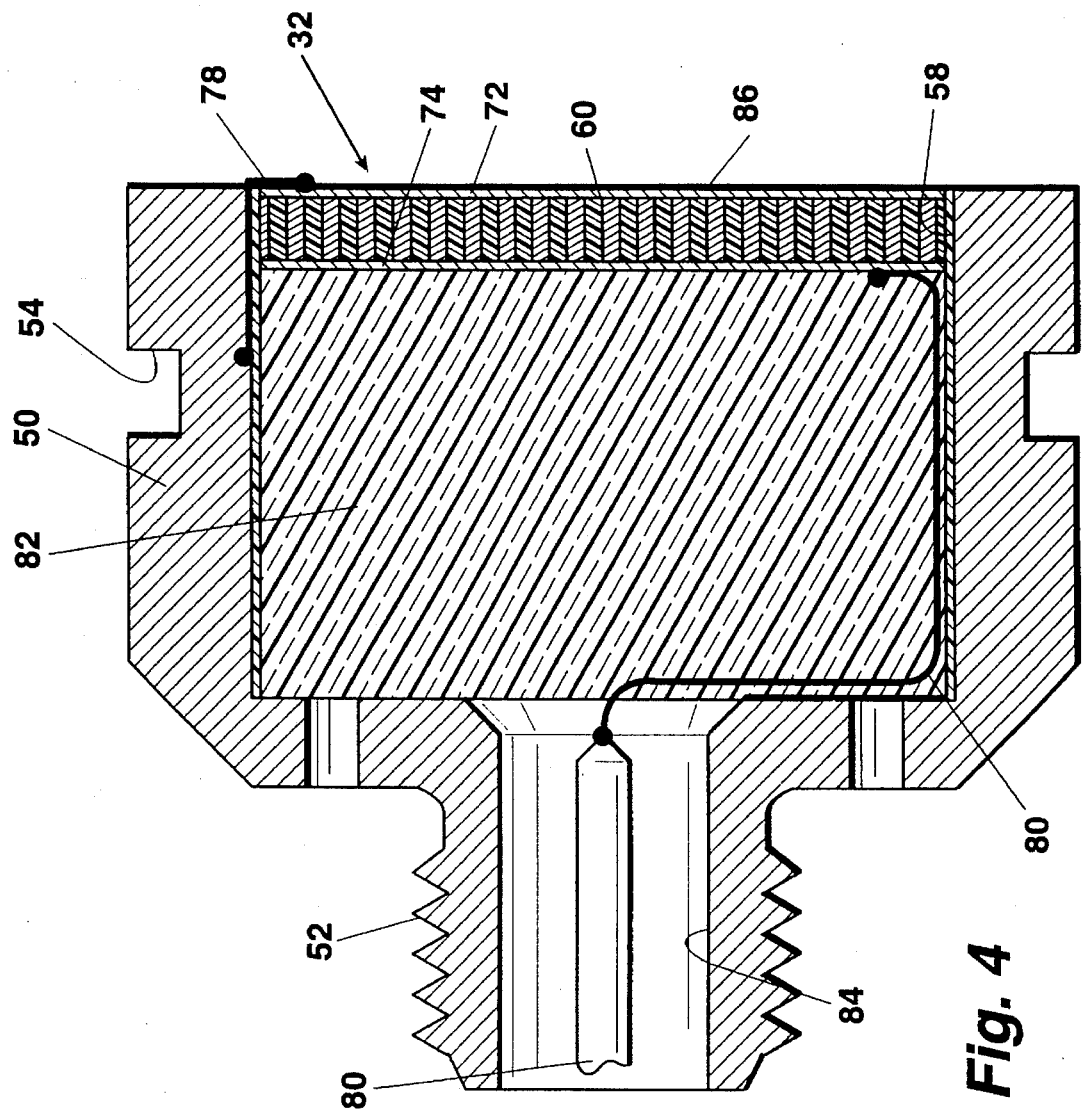
FIG. 4 is a cross-sectional view, greatly enlarged, of one of the multi-element transducers that is employed in the instrument pig of FIGS. 1 and 2.

FIG. 3 shows an enlarged plan view of a transducer 32, and FIG. 4 is an enlarged cross-sectional view of FIG. 3. As seen in FIGS. 3 and 4, each transducer 32 is formed of a transducer housing 50 having an integral reduced diameter portion 52 that is externally threaded.

Transducer housing 50 has a cylindrical cavity 58 into which are positioned the elements that produce ultrasonic energy pulses in response to electrical pulses and which convert reflected ultrasonic energy into electrical signals. The active element within transducer body cavity 58 is a multi-element transducer crystal, generally indicated by numeral 60. This transducer crystal is shown in enlarged isometric view in FIG. 5 and cross-sectional view in FIG. 6. The multi-element crystal 60 is formed of a plurality of rod-like piezoelectric ceramic elements 62. Each of the piezoelectric rod-like elements 62, an example being illustrated in FIG. 5A, is formed of a ceramic piezoelectric material, a commonly employed type being referred to "PZT" standing for "Lead Zirconate Titanate". The rod-like piezoelectric ceramic element 62 has side walls 64, a top face 66 and bottom face 68. The multi-element crystal 60 is formed by positioning a plurality of the rod-like elements 62 so that side walls 64 are adjacent each other but separated by a polymer, and the top faces 66 are in a common surface, and bottom faces 68 are also in a common surface. To support the crystal elements 62 in relationship to each other, a filler material, such as a polymer, is used to fill the voids between the crystal elements. Polymer 70 may be a hard setting epoxy or other high viscosity polymeric material. A commonly employed means of creating a multi-element crystal 60, such as illustrated in FIGS. 4, 5, and 6, is to saw or dice a monolithic crystal to remove portions of the monolith, leaving the rod-like piezoelectric ceramic elements standing in spaced relationship. The void left by the sawing operation is filled with filler 70. The top surfaces 66 and bottom surfaces 68 are then smoothed to provide a uniform, but not necessary planar surface.

A top conductive metal film 72 is applied to the assembly to electrically connect the top surface 66 of each crystal element 62. In like manner, a bottom conductive film 74 is applied to electrically engage bottom surface 68 of each crystal element 62.

Top film 72 provides electrical continuity with top surface 66 of each crystal element 62. In FIG. 5, an electrical signal source 76 has conductors 78 and 80 that extend to top film 72 and bottom film 74 respectively. As seen in FIG. 4, a sound absorbing medium 82 is used to fill the space within cavity 58 of transducer housing 50. The function of the sound absorbing medium 82 is, as the term implies, to absorb sonic energy that otherwise would be reflected from the bottom of housing 50 causing the generation of acoustic noise that would corrupt transmitted acoustic energy and interfere with the energy emitted from top surfaces 66.

As seen in FIG. 4, electrical continuity is applied between housing 50 and top film 72 as diagrammatically illustrated by conductor 78. Conductor 80 attaches to bottom film 74 and extends out of the transducer housing through an electrical connector 84 and is passed to instrumentation 34 as seen in FIG. 1.

After the multi-element crystal 60 with top and bottom films 72 and 74, along with sound absorbing material 82 is assembled in cavity 58 of transducer housing 50, protective layer 86 is applied over top film 72 and over the outer end of housing 50. Protective layer 86 serves the dual function of helping to match the impedance of the multi-element transducer 60 with that of the couplant media, that is, the fluid flowing in the pipeline, and also to provide a sealed closure of the transducer to prevent penetration of fluid into the interior of cavity 58 caused by either elevated pressures or temperatures.

The advantage obtained by the use of the multi-element piezoelectric crystal arrangement of each of the transducers as has been described is best understood by reference to FIGS. 7 through 14.

Figure 8A:
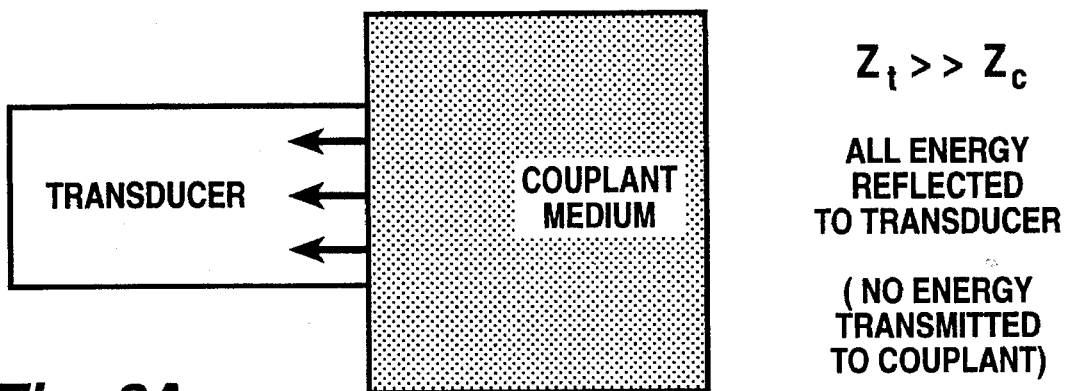
FIG. 8A is a diagrammatic illustration showing the effect of transmission of acoustic energy from a transducer to a couplant medium wherein the acoustic impedances of the couplant medium and the transducer are greatly mismatched, showing that substantially all sonic energy produced by the transducer is reflected back into the transducer and substantially none into the couplant media.
Figure 8B:
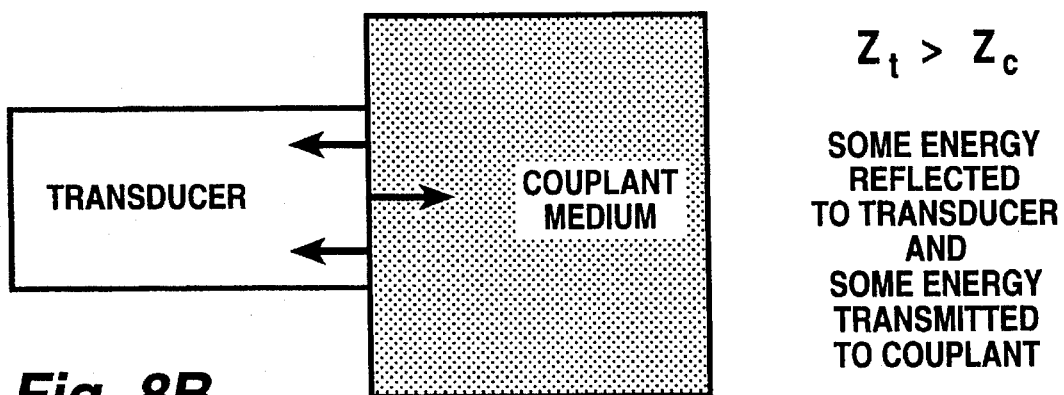
FIG. 8B shows diagrammatically the relationship where the couplant medium impedance is somewhat closer to that of the transducer so that some of the energy of an ultrasonic pulse produced by the transducer is transmitted into the couplant.
Figure 8C:
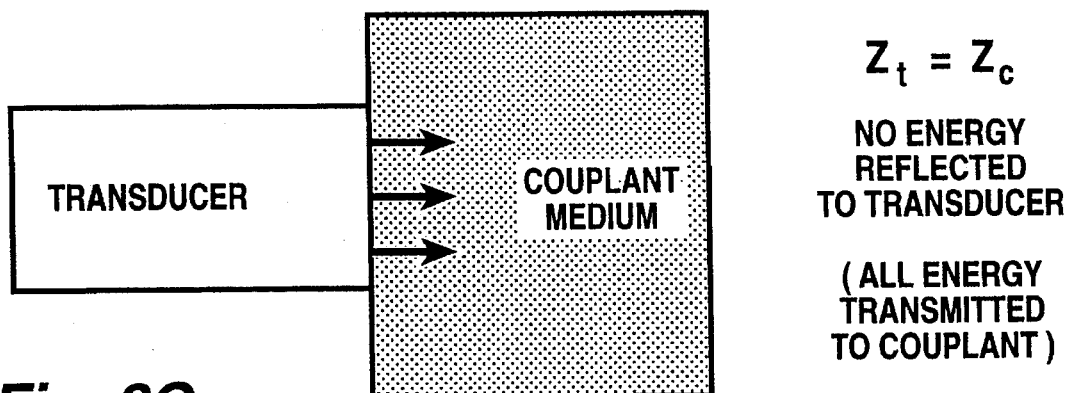
FIG. 8C shows the ideal situation in which the couplant acoustic impedance matches the transducer acoustic impedance in which a maximum portion of the energy of a sonic pulse is transmitted from the transducer into the couplant medium.

First, FIGS. 8A, 8B and 8C illustrate the need for a transducer used in a pipeline inspection pig to have the capability of generating sonic energy that is effectively coupled into the couplant media. As illustrated in FIGS. 8A, 8B and 8C, the amount of sonic energy that can be delivered from a transducer to a couplant is directly related to the relative acoustic impedances of the couplant and the transducer. The designer of an instrumentation pig for pipeline inspection frequently has no choice in the couplant, that is, the couplant is whatever fluid, whether liquid or gas, that the pipeline is transporting. Thus, it is critical that the designer of the pipeline inspection pig choose a transducer structure that matches the acoustic impedance of the couplant as closely as possible.

Figure 13:
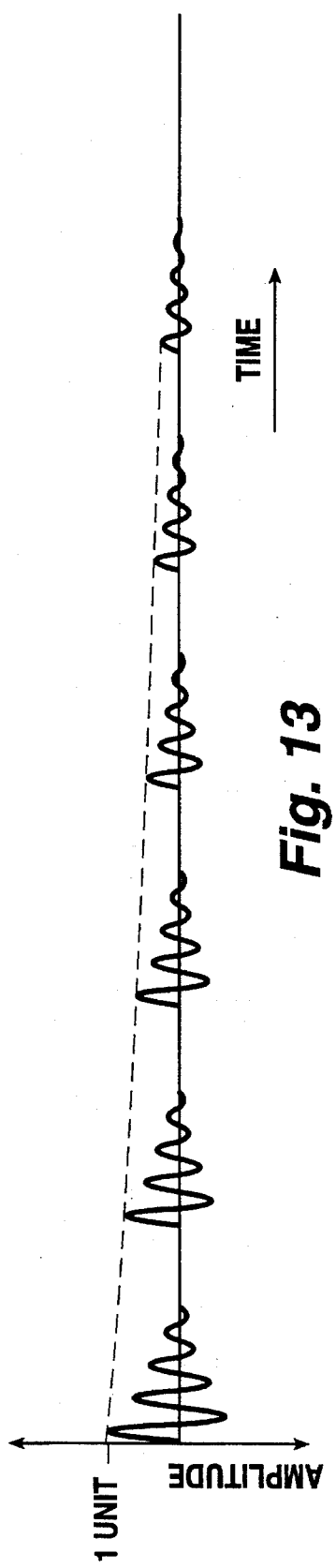
FIG. 13 shows the typical situation wherein a monolithic crystal is used in a transducer for pipeline inspection in which a relative weak ultrasonic signal is transmitted by the transducer into the couplant to impinge on the pipe inside and outside walls. This figure shows the relatively fast decay that results from the relatively weak ultrasonic signal generated by the transducer that is transmitted by the couplant.
Figure 14:
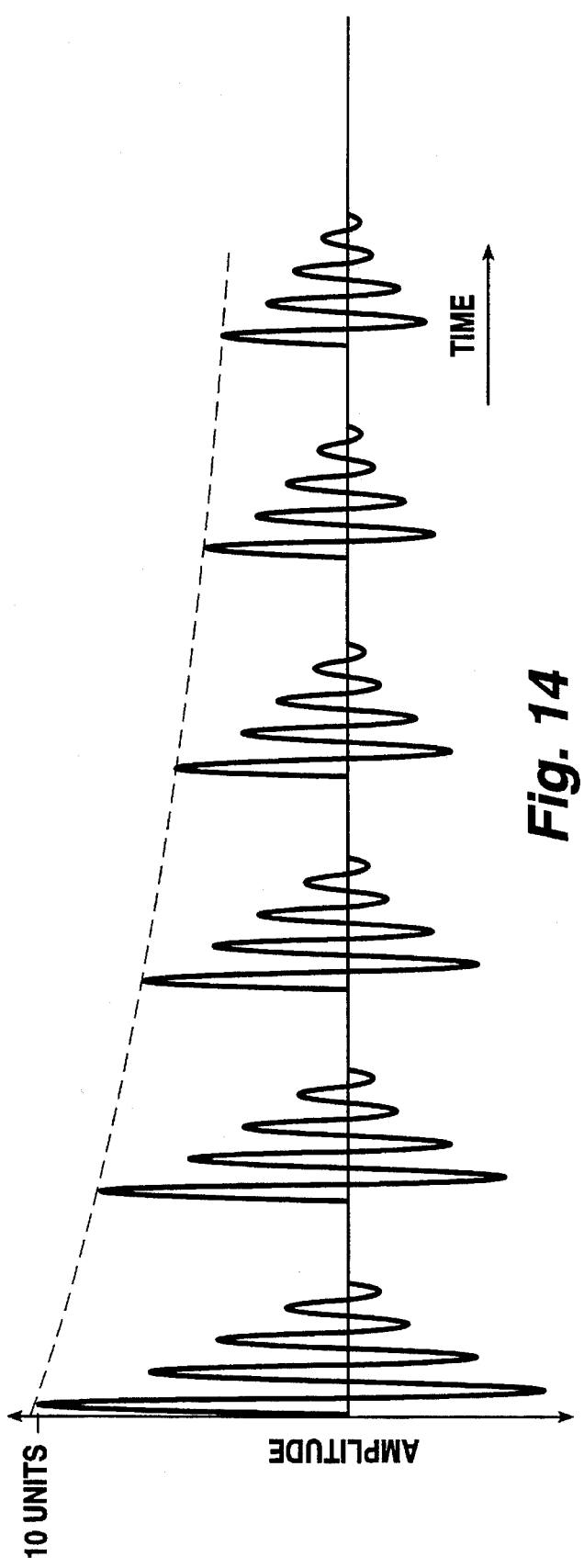
FIG. 14 is a diagram of electrical signals as shown in FIG. 13 but showing signals resulting from the use of a multi-element transducer of the type illustrated in FIGS. 4, 5 and 6. This diagram, when compared to FIG. 13, shows the relatively slower decay of the reflective signals and illustrates the arrangement whereby multiple OD reflections can be utilized in response to each ultrasonic pulse for determining a pipe wall thickness.

Applicants have discovered that multi-element transducers can be tailored for acoustic impedance matching with the majority of pipeline fluids, heretofore not possible with monolithic ceramic transducer technology. FIGS. 13 and 14 represent an evaluation of applicants' invention comparing a specified multi-element transducer 32 to the best effort monolithic transducer obtainable. Acoustic wave forms represented on the plots were produced under exact same conditions with the only difference being the type of transducer technology used. The first wave form located at the left of each of the plots is acoustic energy converted to electrical energy from the acoustic energy reflected from the interior pipe wall. The subsequent wave forms are energy reflected from the exterior pipe wall. Multiple exterior pipe wall wave forms are seen because of reverberation of acoustic energy reflecting from ID pipe wall/fluid high impedance interface to OD pipe wall/material surrounding pipe high impedance interface within the pipe wall itself. Some acoustic energy enters the couplant and is directed towards the transducer. In a multiple signal processing inspection pig, for example, several return echoes are used to discern pipe wall information, that amplitude of the last return is critical for accurate data analysis.

The acoustic impedance of a multi-element transducer can be adjusted by choosing appropriate PZT material, geometric configuration of the elements, ratio of ceramic to polymer phase, choice of matching impedance layer material, and thickness of active materials contained within the transducer including, but not exclusive to, the multi-element active ceramic.

Because the multi-element transducers can be geometrically configured in virtually an infinite number of ways, the applicants found that by varying the geometric shapes of the rod-like ceramic elements 60, the interstitial spacing and the resin filler material 70 the transducers could be designed such that their acoustic impedance's would more closely match that of any given couplant fluid. This provides a means whereby a transducer can be specially designed for application in any known pipeline fluid. While the acoustic impedance achieved for a specific transducer design may not match perfectly with the impedance of the target couplant fluid, the match is close enough to provide greatly enhanced performance in terms of the energy transmitted and the electrical signals received by the transducers. This flexibility in transducer design allows for a kind of "designer" transducer to be produced for all common pipeline fluids from heavy crude oils to natural gas. Indeed, once the properties of the transported fluid in a given pipeline are known, an inspection system can be fitted with an array of transducers designed specifically for that fluid. Under such circumstances, the performance of the inspection system will be significantly improved in comparison with that where a conventional monolithic transducer is used in the inspection process.

Figure 7:
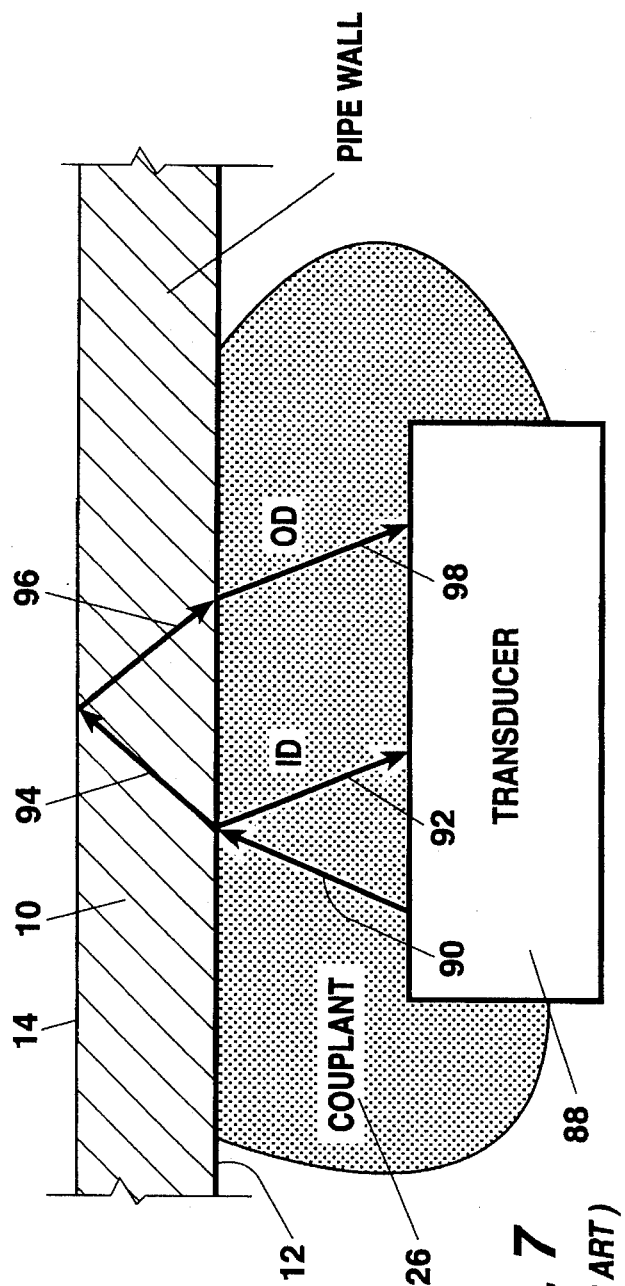
FIG. 7 illustrates a traditional transducer that employs a monolithic crystal as used in a pipeline inspection pig and shows diagrammatically the coupling of an acoustic pulse from the transducer through the couplant, that is, the fluid that flows in the pipeline, to the pipeline interior wall, through the pipe to the exterior wall, and the reflection back from the exterior wall to the transducer.

FIG. 7 shows the results of using a transducer 88 that is capable of imparting a relatively weak ultrasonic signal into couplant 26. Transducer 88 is typical of the monolithic transducers previously employed in which an ultrasonic pulse 90 is transmitted in couplant 26 (pipeline fluid or gas) to impinge upon the inside diameter 12 of pipe 10. Part of this ultrasonic energy is reflected directly back to the transducer, the reflective portion being indicated by the numeral 92 and a part of the signal 94 is transmitted through pipe 10 and reflected from outside wall 14, the outside reflected signal within the pipe being indicated by the numeral 96. When signal 96 reaches the interior surface 12 of the pipe, part of it is passed by the couplant 26 back through the transducer, such signal being indicated by the numeral 98.

Figure 10:
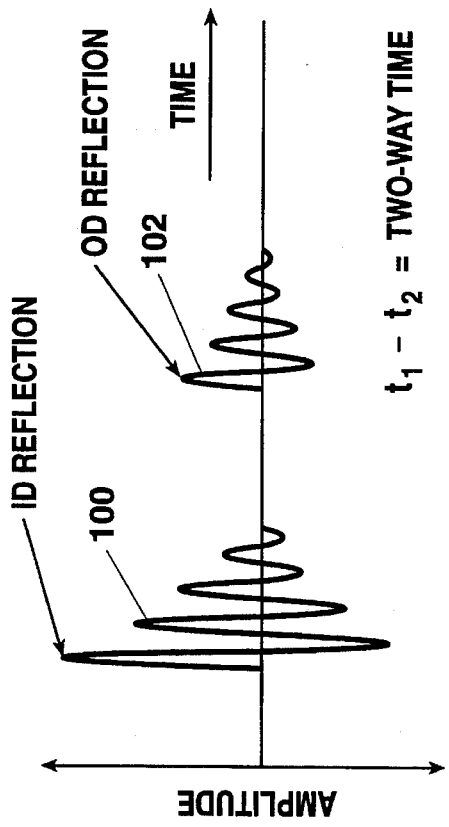
FIG. 10 is a diagram showing electrical signals obtained as a response from the transducer arrangement of FIG. 7 in which a signal is received from the pipe inner wall and a single signal from the pipe exterior wall. The time difference between these two signals is substantially equal to twice the time of travel of sound between the ID and OD of the pipe, thus, permitting a calculation of the pipe wall thickness.

FIG. 10 shows the electrical signal that can be generated in response to the arrangement of FIG. 7. A first electrical signal 100 is indicative of the ID reflected signal 92 of FIG. 7, while the second reflected signal 102 is generated in response to acoustic signal 98. By measuring the time difference between signals 100 and 102, it is possible to compute the thickness of pipe 10 by knowing the speed of sound transmission within the pipe material divided by two (the time must be divided by two since signals 94 and 96 travel two times through the thickness of the pipe). The simplistic system of FIGS. 7 and 10 provides only one opportunity for calculating the pipe wall thickness and thus, any error in this single calculation will provide a false reading.

Figure 9:
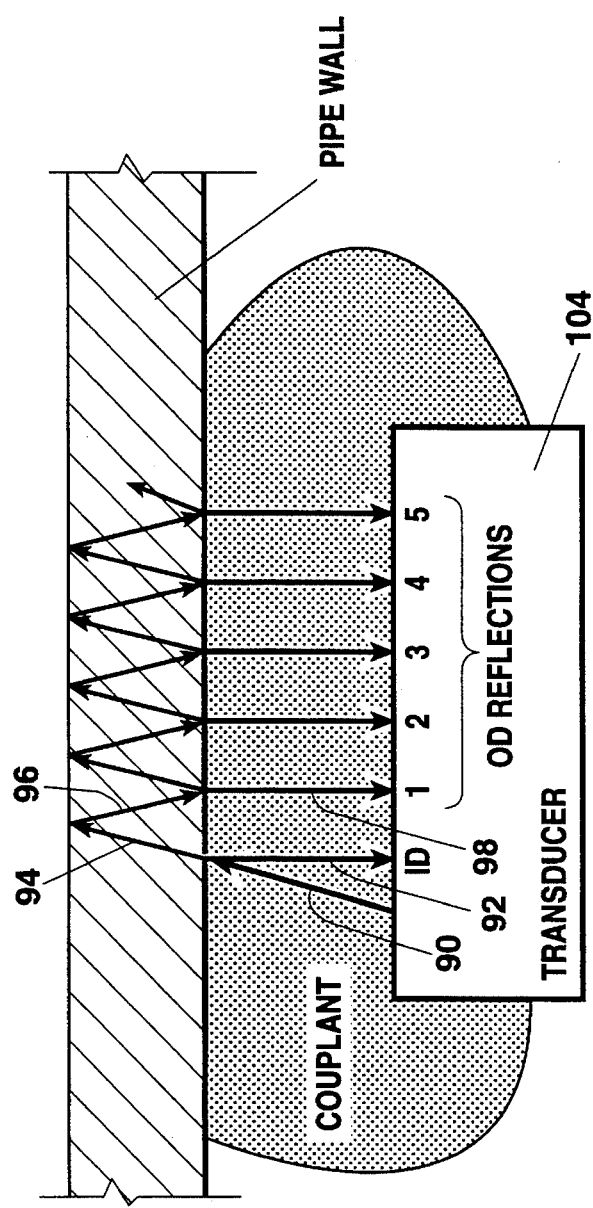
FIG. 9 is a diagrammatic representation of a transducer, such as that carried by an instrumentation pig in a pipeline, as was described with reference to FIG. 7, but showing the situation in which the ultrasonic transducer is capable of transmitting a sonic energy pulse with sufficient amplitude to cause multiple reflections between the interior and exterior pipeline wall, that is, between the ID and OD of the pipe to thereby cause a plurality of OD reflections that are transmitted back to the transducer. By employing a plurality of signals obtained from reflections within the pipe between the inside and outside walls, the characteristic of the pipe and, particularly, the thickness of the pipe wall can be more accurately determined.
Figure 11:
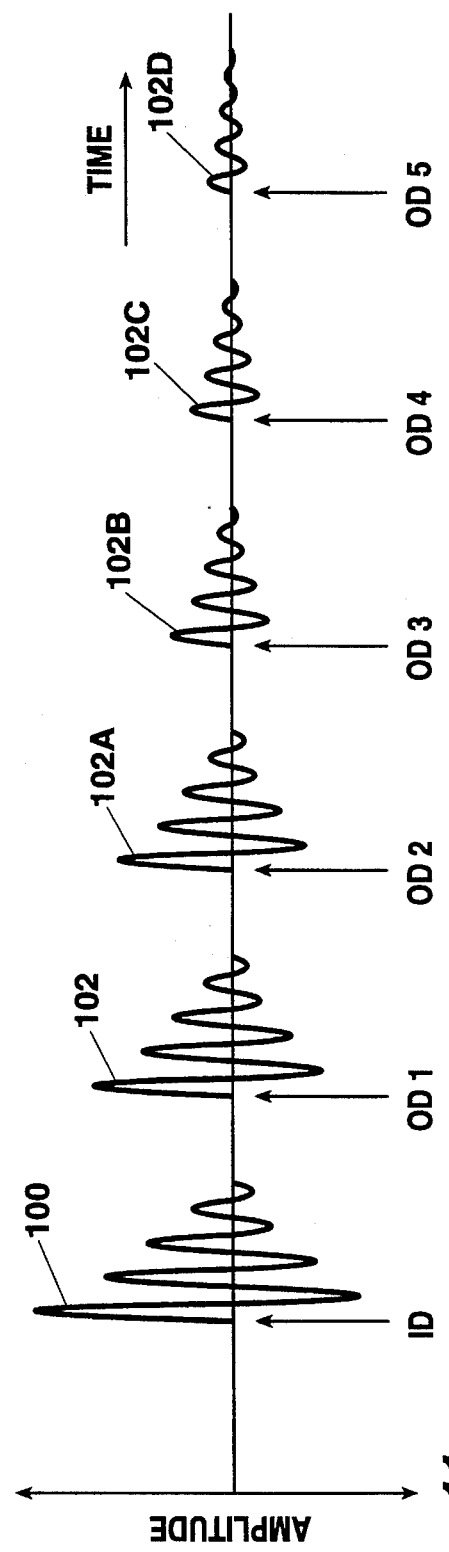
FIG. 11 shows the signal pattern as derived from the arrangement of FIG. 9 wherein multiple OD reflections can be used to calculate the pipe wall thickness.

FIGS. 9 and 11 show the advantages achieved by the use of a properly designed multi-element transducer 104. The initial ultrasonic signal 90, as previously described, produces signals 92, 94, 96 and 98. However, when an ultrasonic signal is generated by transducer 104 a plurality of useable signals are received at the transducer. The plurality of additional reflected signals from the outside wall are indicated by OD2; OD3, OD4 and OD5. These acoustic signals are shown as represented by electrical signals in FIG. 11. The first reflected signal is from the inside wall and is indicated by electrical signal 100, and the first outside wall reflected acoustic signal is represented by electrical signal 102 as previously described. The additional outside pipe wall electrical signals are represented by 102A, 102B, 102C and 102D. By measuring the time between ID and OD1; between OD1 and OD2; between OD2 and OD3; between OD3 and OD4; and between OD4 and OD5, several opportunities are presented for determining the pipe wall thickness. But more importantly, it facilitates the use of the measurement algorithm that can eliminate ambiguities in measurement.

Figure 12:
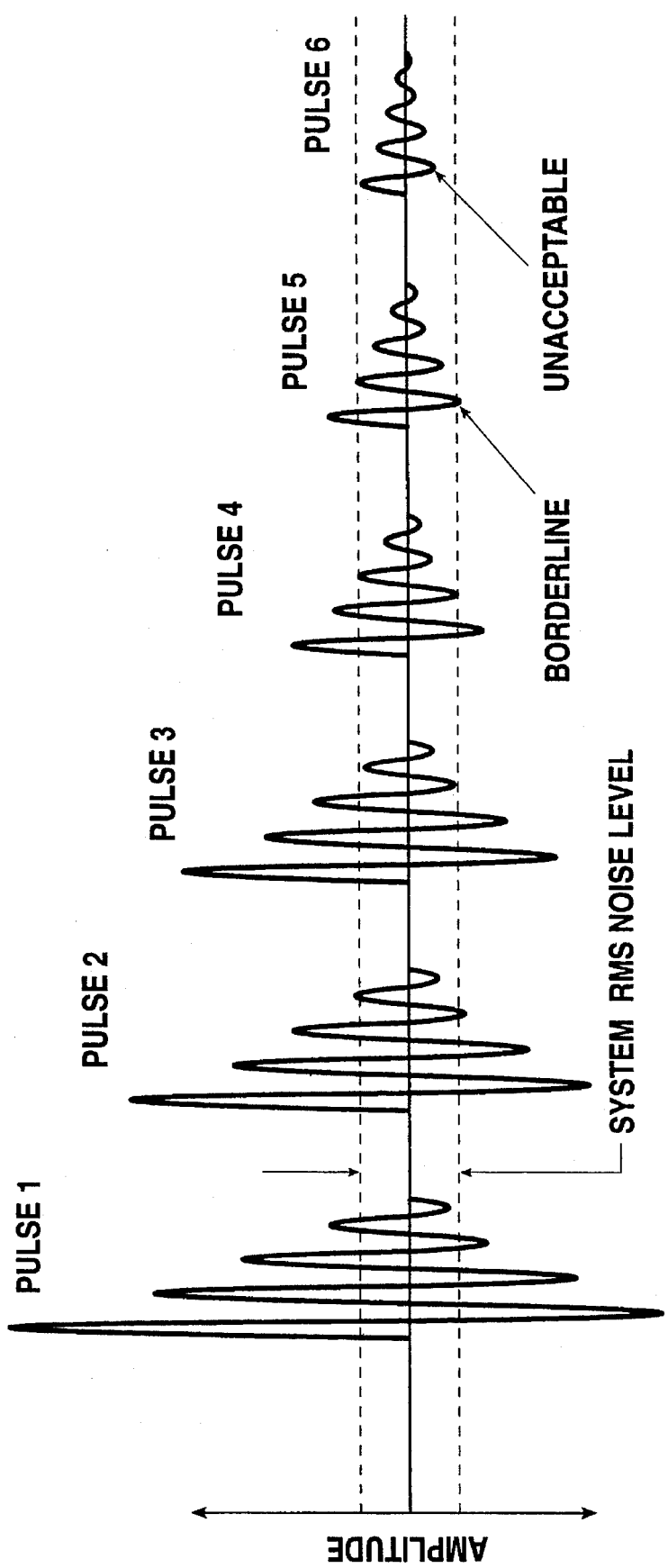
FIG. 12 is a graph showing electrical signals similar to that shown in FIG. 11 wherein Pulse 1 is the ID signal, Pulse 2 is the first OD signal, Pulse 3 is the second OD signal and so forth.

It is well known in the field of electronics that only those signals exceeding background noise of a data gathering system can be detected and used to achieve the data gathering system functions. FIG. 12 illustrates the arrangement wherein typical instrumentation has the capability of responding to received signals above a preselected amplitude indicated in FIG. 12 by "System RMS Noise Level", "RMS" referring to "Root Means Square" or a technique for measuring the value of an alternating electrical signal. In the arrangement of FIG. 12, it can be seen that Pulses 1 through 5 are all above the system background noise level and are, therefore, useful in calculating pipe wall thickness. Pulse 6 falls below such level and would not be useful. FIG. 12 further illustrates the importance of being able to generate acoustic pulses of sufficient magnitude to provide multiple opportunities with each pulse to measure pipe wall thickness.

FIG. 13 shows how rapidly signals produced by transducers poorly matched to the couplant impedance decrease, that is, electrical signals produced by monolithic transducers. FIG. 14 shows by comparison how a specially designed multi-element transducer produces a much better signal due to better impedance matching. Multi-element transducers of the type illustrated and described with reference to FIGS. 3 through 6, provide electrical signals representing multiples in pipe or "metal time" reflections to thereby increase the opportunity for accurately determining pipe wall thickness.

As the pipeline pig 18 moves through a pipeline, each of the multi-element transducers 32 produces a sonic pulse at a preselected rate, such as approximately 200 times per second, and each receives a reflected pulse train indicating several transmissions between the interior and exterior OD of the pipe. The received pulse trains are analyzed by on-board data processing, a part of which utilizes an algorithm to determine pipe wall characteristics. The computer program employed in instrumentation 34 can be arranged to eliminate from data storage the results of all measurements wherein the pipe wall is found to be within the manufactured thickness and to record for final analysis only the instances wherein the pipe wall is found to be of less thickness than that anticipated, such as when the measurement is made at an area of corrosion 16 as shown in FIG. 1. By coordinating a detected anomaly in the pipe wall thickness with the position of the pig in the pipeline as determined by odometer 36, (FIG. 1) the operator will know that a potential problem exists and find the defect location, above ground in the pipeline. Above ground defect location is commonly known as a "dig site" or "excavational site". If the potential problem is of significant severity or interest, the operator can excavate the pipeline for a visual inspection of the damaged area if the defect is external. Interior defects can be verified via external ultrasonic tests, radiography (x-rays), and pipe removal if necessary.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of providing a record that can be used to determine the characteristics of the wall of a pipeline, the pipeline having a fluid media therein, the fluid media having a known acoustic impedance, comprising:

passing an instrument pig through the interior of the pipeline having said fluid media therein;

by means of a plurality of spaced apart multi-element transducers carried by said instrument pig, generating a sequence of transducer initiated ultrasonic pulses, each ultrasonic pulse being coupled from a said multi-element transducer to said fluid media and thereby to the pipeline interior wall and through the pipeline from the interior wall to the exterior wall, a portion of the acoustic pulse being reflected by both the pipeline interior and exterior walls to provide detectable interior and exterior pipeline wall reflected acoustic pulses that are coupled by said fluid media back to said transducer;

generating electrical signals in said multi-element transducers as a consequence of said interior and exterior pipe wall reflected acoustic pulses; and analyzing said electrical signals to provide information as to the characteristics of a pipe wall.

2. A method of providing a record that can be used to determine the characteristics of the wall of a pipeline according to claim 1 wherein each said multi-element transducer is arranged so that each said transducer initiated ultrasonic pulse is of a magnitude to cause a sequence of reflections of the ultrasonic pulse between said pipeline interior and exterior walls, a portion of each reflection being reflected back to said transducer where it is converted into a corresponding electric signal, thus producing for each said transducer initiated acoustic pulse an electrical pulse train consisting of an interior pipe wall reflection with sequential exterior pipe wall reflections that can be analyzed to provide information as to the characteristics of the pipe wall.

3. A method of providing a record that can be used to determine the characteristics of a pipeline according to claim 1 wherein each said multi-element transducer has an internal acoustic impedance that is in proximity to the acoustic impedance of said fluid media.

4. Apparatus for determining the wall thickness of a pipe having fluid therein, the pipe having an interior wall and an exterior wall, the fluid having a known acoustic impedance, comprising:

a housing;

fluid sealing means associated with said housing to cause said housing to travel through said pipe by the force of fluid flow;

odometer means providing odometer electrical signals response to the travel of said housing in a pipe;

a plurality of multi-element transducers attached to said housing that transmit acoustic pulses into said pipe and receive reflected acoustic signals from said interior wall and exterior wall of said pipe;

circuit means contained within said housing to cause transmission of said acoustic pulses and to provide electrical indicator signals in response to said reflected acoustic signals, which electrical indicator signals have a direct relationship to the distance between said interior wall and said exterior wall of said pipe;

means to record said electrical indicator signals in relationship to said odometer signals;

each of said multi-element transducers being comprised of a plurality of discrete piezoelectric elements with a polymer fill between the elements, the piezoelectric elements having sidewalls arranged in adjacent mechanically isolated relationship with each other providing interstices therebetween, each piezoelectric element having a forward face and a rearward face, the interstices being filled with a viscous polymer;

a first conductive film in electrically continuity with each said piezoelectric element forward face;

a second conductive film in electrical continuity with each said piezoelectric element rearward face; and conductors connecting said first and second films to said circuit means.

5. An apparatus according to claim 4 wherein each said multi-element transducer has an internal acoustic impedance that closely matches said known acoustic impedance of said fluid.

6. A method of measuring the wall thickness of a pipe having an interior and exterior wall employing a pig body having a circumferential surface and having fluid sealing means to cause the pig body to travel through the pipe by the force of a fluid flowing in the pipe, the fluid having a known acoustic impedance, comprising:

(a) mounting on said pig body circumferential surface a plurality of multi-element transducers in spaced apart relationship, each transducer having a plurality of discrete piezoelectric rod-like elements each having sidewalls, a forward face and a rearward face, the plurality of rod-like elements separated by a polymer being arranged so that their sidewalls are in adjacent and mechanically isolated relationship, said rod-like elements presenting said forward faces thereof in a common surface and presenting said rearward faces thereof in a common surface, a first conductive film being secured to said forward faces of said rod-like elements and a second conductive film being secured to said rearward faces of said rod-like elements;

(b) by means of a circuit carried by said pig body, sequentially transmitting an electrical pulse in the form of a voltage differential between said first and second conductive films of each of said multi-element transducers to cause each said multi-element transducer to initiate an ultrasonic pulse in said fluid flowing in said pipe, ultrasonic pulses being reflected by said pipe interior and exterior walls, the reflected ultrasonic pulses impinging on said multi-element transducers;

(c) in each multi-element transducer, converting said reflected ultrasonic pulses to electric signals; and (d) analyzing said electrical signals to provide a measurement of said pipe wall thickness determined by the time lapse between said ultrasonic pulses reflected by said pipe interior and exterior walls.

7. A method according to claim 6 wherein said pig body has an odometer that provides an electrical signal indicating the travel of said pig body in said pipe and including the step of comparing said indication of pipe wall thickness of step (d) with said electrical signal indicating the travel of said pig body to indicate the location of a said indication of said pipe wall thickness.

8. A method of measuring the wall thickness of a pipeline according to claim 6 wherein the step of mounting on said pig body circumferential surface a plurality of multi-element transducers includes the step of mounting multi-element transducers each of which is designed to have an internal impedance that is compatible with said known acoustic impedance of said fluid, regardless of the specific acoustic properties of said fluid.

\* \* \* \* \*